United States Patent [19]
Ke et al.

[11] Patent Number: 5,221,696
[45] Date of Patent: Jun. 22, 1993

[54] USE OF MONOACYL PHOSPHOGLYCERIDES TO ENHANCE THE CORNEAL PENETRATION OF OPHTHALMIC DRUGS

[75] Inventors: Tai-Lee Ke, Grand Prairie; Eugene R. Cooper, Crowley; Douglas F. Hager, Fort Worth; Jamieson C. Keister, Crowley, all of Tex.

[73] Assignee: Alcon Laboratories, Inc., Fort Worth, Tex.

[21] Appl. No.: 651,886

[22] Filed: Feb. 7, 1991

Related U.S. Application Data

[63] Continuation of Ser. No. 329,924, Mar. 29, 1989, abandoned.

[51] Int. Cl.$^5$ .................... A61K 47/00; A61K 31/685
[52] U.S. Cl. ........................................ 514/786; 514/78; 514/788; 514/912; 514/947
[58] Field of Search ................ 514/78, 912, 786, 788, 514/947

[56] References Cited

FOREIGN PATENT DOCUMENTS

PCT/GB88/-
00396 5/1988 PCT Int'l Appl. .

OTHER PUBLICATIONS

"Permeability of Rabbit Corneal Epithelium to Horseradish Peroxidase After the Influence of Benzalkonium Chloride," Tonjum, *Acta Ophthalmologica*, vol. 53, pp. 335–347 (Jan., 1975).

"Evaluation of Permeability Enhancement of Hydrophilic Compounds and Macromolecular Compounds by Bile Salts Through Rabbit Corneas In Vitro," Morimoto, *J. Pharm. Pharmacol.*, 39: 124–126 (Jul., 1986).

"Ophthalmic Compositions Containing Biphenamine and Their Use in the Treatment or Prevention of Inflammation," Schulte, *Chemical Abstracts*, 106: 125931t, vol. 106 (1987).

"Mechanisms of corneal Drug Penetration 1: In Vivo and In Vitro Kinetics," Grass, *Journal of Pharmaceutical Sciences*, vol. 77, No. 1., (Jan. 1988).

"Topically Applied Cyclosporine in Azone Prolongs Corneal Allograft Survival," Newton et al., *Investigative Ophthalmology and Visual Science*, vol. 29, No. 2, pp. 208–215 (Feb., 1988).

*Primary Examiner*—Frederick E. Waddell
*Assistant Examiner*—Zohreh A. Fay
*Attorney, Agent, or Firm*—James A. Arno; Sally S. Yeager

[57] ABSTRACT

The use of monoacyl phosphoglycerides to enhance the penetration of topically applied ophthalmic drugs through the corneal epithelium is described.

22 Claims, 2 Drawing Sheets

USE OF MONOACYL PHOSPHOGLYCERIDES TO ENHANCE THE CORNEAL PENETRATION OF OPHTHALMIC DRUGS

This application is a continuation of U.S. Ser. No. 07/329,924 filed Mar. 29, 1989 now abandoned.

BACKGROUND OF THE INVENTION

The present invention relates to the field of ophthalmic drug delivery. More particularly, this invention relates to enhancement of the penetration of ophthalmic drugs and other therapeutic agents through the cornea of the eye.

In order for an ophthalmic drug to be therapeutically effective, it is generally necessary for the drug to penetrate the cornea and be taken up in the aqueous humor, ciliary processes and other tissues in the eye. There are notable exceptions to this general rule, such as drugs or drug products which produce a therapeutic effect by acting on the exterior surface of the cornea (e.g., drugs or drug products useful in improving ocular comfort and/or treating dry or irritated eyes). However, the treatment of conditions involving physiological mechanisms within the eye (e.g., glaucoma, diabetic retinopathy, cataracts, etc.) generally does require the movement of topically applied ophthalmic drugs through the cornea.

In order for a drug to pass through the cornea, it must penetrate three layers of tissue, namely, the epithelium, stroma and the endothelium. Except for highly lipophilic drugs, the epithelium is the main barrier to drug penetration of the cornea. Penetration of the stroma basically involves diffusion of the drug through a barrier which is approximately 360 microns thick. There are currently no known methods of enhancing drug penetration through the stroma or endothelium. However, it is possible to enhance the penetration of drugs through the epithelium, and thereby enhance the overall absorption of drugs applied topically to the eye. The present invention is directed to such enhancement.

There have been prior attempts to enhance the penetration of drugs through the corneal epithelium. The goal of such attempts has generally been to enhance penetration of drugs through the corneal epithelium to an optimal point at which the stroma alone controls drug transport through the cornea. The prior attempts have included use of chemical agents to enhance the penetration of drugs through the epithelium. It has been reported that benzalkonium chloride (BAC), bile salts, dimethyl sulfoxide (DMSO), ethylenediamine tetraacetate (EDTA) and 1-dodecylazayl-cycloheptan-2-one (AZONE®) enhance the corneal penetration of certain drugs. The following publications may be referred to for further background concerning the use of such agents to enhance corneal penetration: *Acta Ophthalmological*, Vol.53, p.335 (1975); *J. Pharm. Pharmacol.*, Vol.39, p.124 (1987); *Chem. Abstracts*, Vol.106, 125931t, p.402 (1987); *Journal of Pharmaceutical Sciences*, Vol.77, No.1 (Jan.,1988); and *Investigative Ophthalmology and Visual Science*, Vol.29, No.2 (Feb.,1988). Notwithstanding such prior attempts, there continues to be a need for a means of safely and effectively enhancing the penetration of drugs through the cornea.

SUMMARY OF THE INVENTION

A principal objective of the present invention is to provide for a method of enhancing the ability of drugs and therapeutic agents to penetrate the cornea. A further objective of the present invention is to provide topical ophthalmic compositions containing one or more agents for enhancing the corneal penetration of the active ingredient(s) contained therein.

The foregoing objectives and other general objectives of the present invention are satisfied by the provision of a means of enhancing corneal penetration by using a class of compounds referred to herein as "monoacyl phosphoglycerides" to enhance the penetration of ophthalmic drugs through the corneal epithelium. In addition, the objectives of the present invention are furthered when viscosity enhancing polymers are used in conjunction with the monoacyl phosphoglycerides to ensure the monoacyl phosphoglycerides are retained in the eye for a relatively longer period of time, thus allowing the compounds more time to facilitate drug transport through the cornea.

DETAILED DESCRIPTION OF THE INVENTION

Figure 1:
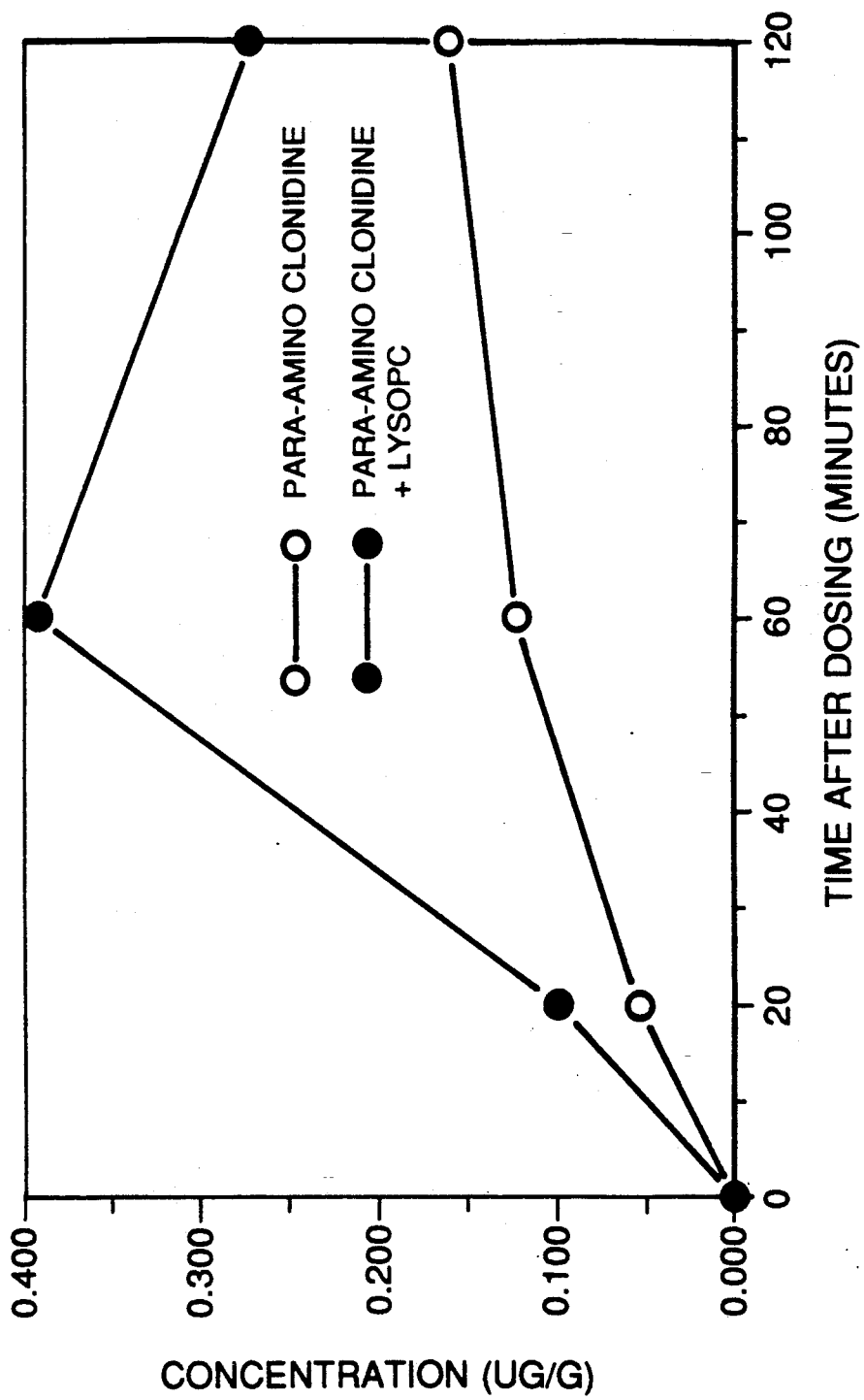
FIG. 1 compares the amount of a drug, para-aminoclonidine, found in the aqueous humor of rabbits which were administered the drug with and without lysophosphatidylcholine C18:0 (Lysopc).

The present invention is based on the discovery that amphipathic monoacyl phosphoglycerides effectively and safely enhance the corneal penetration of ophthalmic drugs. These penetration enhancers can be used in compositions comprising any ophthalmic drug which, to be effective, must be substantially taken up by the aqueous humor, ciliary processes and other tissues in the eye upon topical administration. Examples of classes of ophthalmic drugs with which the monoacyl phosphoglycerides of the present invention can be used, include: steroids, growth factors, cycloplegics, miotics, mydriatics, therapeutic proteins and peptides, antioxidants, aldose reductase inhibitors, nonsteroidal antiinflammatories, immunomodulators, antiallergics, antimicrobials and anti-glaucoma agents.

The penetration enhancing monoacyl phosphoglycerides used in the present invention have the following structure:

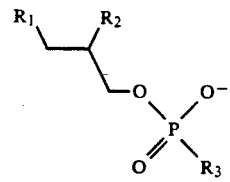

wherein one of $R_1$ and $R_2$ is hydrogen, thiol, hydroxyl, amino, lower alkyl, lower alkoxy (eg. methyl, ethyl, methoxy or ethoxy) or alkyl sulfide and the other is an esterified, etherified or amidified hydrophobic group, and $R_3$ is a hydrophilic group. The preferred hydrophobic groups include saturated and unsaturated aliphatic hydrocarbon groups which range from 14 to 24 carbons in length with zero to 5 double bonds. The aliphatic hydrocarbon groups can be straight or branched chain and may be substituted by one or more aromatic, cycloaliphatic or hydrophilic (e.g. hydroxyl, thiol, or amino) groups. Examples of suitable hydrophilic groups ($R_3$) include O-inositol, choline, O-choline, O-carnitine, O-$(CH_2)_3$-choline, O-glycerol and O-lysophosphatidylglycerol.

The preferred monoacyl phosphoglycerides are lysophospholipids, such as lysophosphatidylcholine, lysophosphatidylinositol, (lysolecithin), lysocardiolipin, lysodesoxylipids, lysophosphorylipids and α-lyso-r-O-alkyl or O-alkenyl phospholipids such as DL-α-Lysolecithin-r-O-hexadecyl and DL-α-Lysolecithin-r-O-alkyl. The most preferred monoacyl phosphoglyceride is 1-acyl lysophosphatidylcholine (C18:0, C18:1, C16:0 or C16:1). The 1-acyl lysophosphatidylcholine C18:0 (lysolecithin) which is most preferred has the following structural formula:

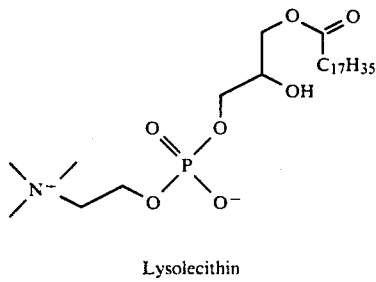

Lysolecithin

The monoacyl phosphoglycerides which are useful in the present invention may be described as being "amphipathic", since they include both hydrophilic and hydrophobic groups. While not wishing to be bound by any theory, it is believed that amphipathic monoacyl phosphoglycerides enhance the corneal penetration of drugs by partition and interaction with protein, glycoprotein and lipid components present in the membrane of the corneal epithelium. Such interaction is believed to alter the degree of order of the proteins and lipids in the membrane, thereby modifying the function of the epithelium as a barrier to drug penetration. Whatever the mechanism, the net result is that drug penetration of the epithelium is enhanced.

The use of monoacyl phosphoglycerides in accordance with the present invention to enhance corneal penetration of drugs significantly increases the amount of drug which is able to penetrate the cornea. The degree of enhancement will vary with different drugs, but in some cases may be as much as 3-fold or more. Because drugs can more effectively penetrate the cornea, less drug is lost due to flow down the punctum and therefore less drug need be administered to effectively treat a particular indication. This is particularly beneficial when it is necessary to administer drugs which cause severe systemic side effects.

The amount of monoacyl phosphoglyceride required in order to enhance corneal penetration will depend on various factors, such as the solubility, partition coefficient and molecular weight of the ophthalmic drug or therapeutic agent; the excipients (surfactants, preservatives, polymers) present in the formulation; and the particular monoacyl phosphoglyceride being used. In general, the more lipophilic the drug to be delivered, the less monoacyl phosphoglyceride is required to enhance penetration, and the higher the concentration of monoacyl phosphoglyceride, the better the corneal penetration. Typically, one or more monoacyl phosphoglycerides will be used in an amount of from about 0.001% to about 0.5% (weight/volume) preferably from about 0.01 to 0.1%.

The monoacyl phosphoglycerides can be used in any topical drug delivery system wherein an excipient or vehicle will not substantially impair or prevent the monoacyl phosphoglycerides from functioning as corneal penetration enhancers. For example, the monoacyl phosphoglycerides can be formulated in compositions which are solutions, suspensions, ointments, gels or films. The type of composition will depend on, among other things, the chemical and physical properties of the drug or therapeutic agent to be delivered. These properties are well known to a person of ordinary skill in the art of drug formulation and delivery.

In a preferred embodiment, the present invention further comprises the use of polymers in conjunction with the monoacyl phosphoglycerides to enhance ocular bioavailability. The longer a topical ophthalmic formulation is in contact with the eye the better the ocular bioavailability. Through the use of polymers in conjunction with the above described monoacyl phosphoglycerides the compositions of the present invention are retained on the cornea longer. As a result, the penetration enhancing components of the compositions can more effectively interact with the corneal epithelium to enhance penetration of the desired drugs or therapeutic agents into the eye. It has been found that the use of polymers in conjunction with monoacyl phosphoglycerides can provide for up to about a 9 to 10 fold increase in the amount of drug or therapeutic agent made available to the eye. The effectiveness of the monoacyl phosphoglycerides is improved when the viscosity of the compositions containing the monoacyl phosphoglycerides is increased up to about 1000 centipoise (cps), preferably between about 50 cps. to 300 cps. Polymers are added to provide for this desired viscosity increase.

Any synthetic or natural polymer which will increase viscosity and is compatible with tissues of the eye and the ingredients of the monoacyl phosphoglyceride compositions can be used. Such polymers are referred to herein as "viscosity enhancing, ophthalmically acceptable polymers." Examples include, but are not limited to: natural polysaccharides and gums, such as: alginates, carrageenan, guar, karaya, locust bean, tragacanth and xanthan; and synthetic polymers, such as: carbomer, hydroxyethylcellulose (HEC), hydroxypropylcellulose, hydroxypropylmethylcellulose (HPMC), methylcellulose, polyvinyl alcohol (PVA), polyvinyl pyrrolidone carboxymethylcellulose and agarose. In addition proteins and synthetic polypeptides which enhance viscosity and are ophthalmically acceptable can be used to increase the viscosity of the compositions to provide for better bioavailability. Typically, proteins which can be used include: gelatin, collagen, albumin and casein.

The preferred viscosity enhancing agents are one or more polymers selected from: PVA, HPMC and HEC. The most preferred agent is HPMC. The viscosity enhancing agents are added to provide for compositions with a viscosity of between about 50 and 300 cps.

The preferred method for enhancing the penetration of a drug or therapeutic agent comprises the use of lysophosphatidylcholine (C18:0) at a concentration of about 0.01% to 0.05% in combination with the polymer HPMC in an amount sufficient to provide a composition with a viscosity of about 50 to about 300 cps.

The following examples further illustrate the compositions which, according to the present invention, comprise monoacyl phosphoglycerides, the corneal penetration enhancing properties of the monoacyl phosphoglycerides and their use to enhance corneal penetration.

EXAMPLE 1

The following formulation is an example of a topical ophthalmic composition which can be used to treat glaucoma.

Formulation

| Ingredients | % (weight/volume) |
| --- | --- |
| Para-amino-clonidine | 0.293* |
| Hydroxypropylmethylcellulose-E50LV, (HPMC)USP | 3.3 |
| Lysophosphatidylcholine (C18:0) | 0.03 |
| Benzalkonium chloride | 0.01 |
| Disodium Edetate, USP | 0.01 |
| Sodium phosphate, monobasic, USP | 0.18 |
| Sodium phosphate, dibasic, USP | 0.12 |
| Mannitol, USP | 3.3 |
| HCl, NF and/or NaOH, NF | q.s. pH to 6.5 + 0.2 |
| Purified Water, USP | q.s. 100 |

*Equivalent to 0.25% + 2% excess para-amino-clonidine as free base.

Preparation

The formulation is prepared in two parts. The hydroxypropylmethylcellulose is first dissolved in purified water to make an approximately 10% solution. This solution is then clarified by filtration and sterilized by autoclaving.

The other ingredients are next dissolved in approximately one-half of the purified water. The mixture is warmed to 40°+5°0 C. for approximately 30 minutes to complete dissolution of the lysophosphatidylcholine. The pH of the solution is adjusted to 6.5 and the solution is sterilized by sterile filtration.

The two solutions are mixed aseptically, stirred, and the remaining purified water is used to bring the solution to final volume.

EXAMPLE 2

Formulation

| Ingredient | Concentration % (w/v) |
| --- | --- |
| Potassium chloride | 0.02 |
| Monobasic postassium phosphate | 0.02 |
| Sodium chloride | 0.80 |
| Dibasic sodium phosphate | 0.216 |
| Lysophosphatidylcholine C18:0 (Lysopc) | 0.03 |
| Para-amino-clonidine | 0.25 |
| Water | q.s. to 100% |

Procedure for Preparation of Formulation

Approximately 85% (8.5 ml) of the batch volume of purified water was added to a container. All of the ingredients were then added to the container: 0.002g potassium chloride; 0.080g sodium chloride; 0.0021g monobasic potassium phosphate; 0.0216g dibasic sodium phosphate; 0.25g para-aminoclonidine. The ingredients were mixed well. 0.003g lysopc was added to the container and sonnicated with heat (30° C.) for 30 minutes. The pH was adjusted to pH 6.0 with 1N HCl (0.20 ml). The solution was then filtered through a sterilizing filter into a sterile receiving vessel. Purified water (q.s. to 10 ml) was then poured through the sterilizing filter and the solution was mixed well.

Twelve New Zealand albino rabbits were selected for evaluation of the penetration through the cornea of the para-amino-clonidine formulation set forth above. All rabbits received 30μl of the 0.25% para-amino-clonidine topically in both eyes. Four rabbits were sacrificed at 20 minutes from dosing and aqueous humor was withdrawn from their eyes. The aqueous humor was assayed by liquid scintillation counting to determine the amount of para-amino-clonidine in the aqueous humor. The same procedure was done on 4 different rabbits at 60 minutes from dosing and on another 4 rabbits, 120 minutes from dosing. Twelve control rabbits received 0.25% para-amino-clonidine as set forth in the formulation above without 0.03% lysopc. Aqueous humor was withdrawn and assayed as explained above. The results are shown in the graph depicted in FIG. 1. It can be seen from the graph that the amount of para-amino-clonidine in the aqueous humor is greater in the rabbits treated with the formulation containing lysopc. At 60 minutes there is almost a four fold increase in the amount of para-amino clonidine found in the aqueous humor of those rabbits which received the drug in conjunction with lysopc versus those who received the drug without lysopc. Therefore, the results indicate that lysopc enhanced penetration of para-amino-clonidine through the cornea.

EXAMPLE 3

Formulation

| Ingredient | Concentration % (w/v) |
| --- | --- |
| Monobasic potassium phosphate | 0.067 |
| Dibasic potassium phosphate | 0.137 |
| Mannitol | 2.45 |
| PVA | 7.0 |
| Lysophosphatidylcholine C18:0 (Lysopc) | 0.03 |
| Para-amino-clonidine | 0.50 |
| Water | q.s. to 100% |

Procedure for Preparation of Formulation

Approximately 85% (8.5ml) of the batch volume of purified water was added to a container. All of the ingredients were added to the container: 0.0067g monobasic potassium phosphate; 0.0137g dibasic potassium phosphate; 0.245g mannitol; 0.7g PVA; 0.05g para-amino-clonidine. The ingredients were mixed well and stirred until all ingredients dissolved into a solution. 0.003g lysopc was added to the container and sonnicated with heat (30° C.) for 30 minutes. The pH was adjusted to pH 6.5 with NaOH. Purified water (q.s. to 10ml) was then poured through a sterilizing filter and the solution was mixed well.

Figure 2:
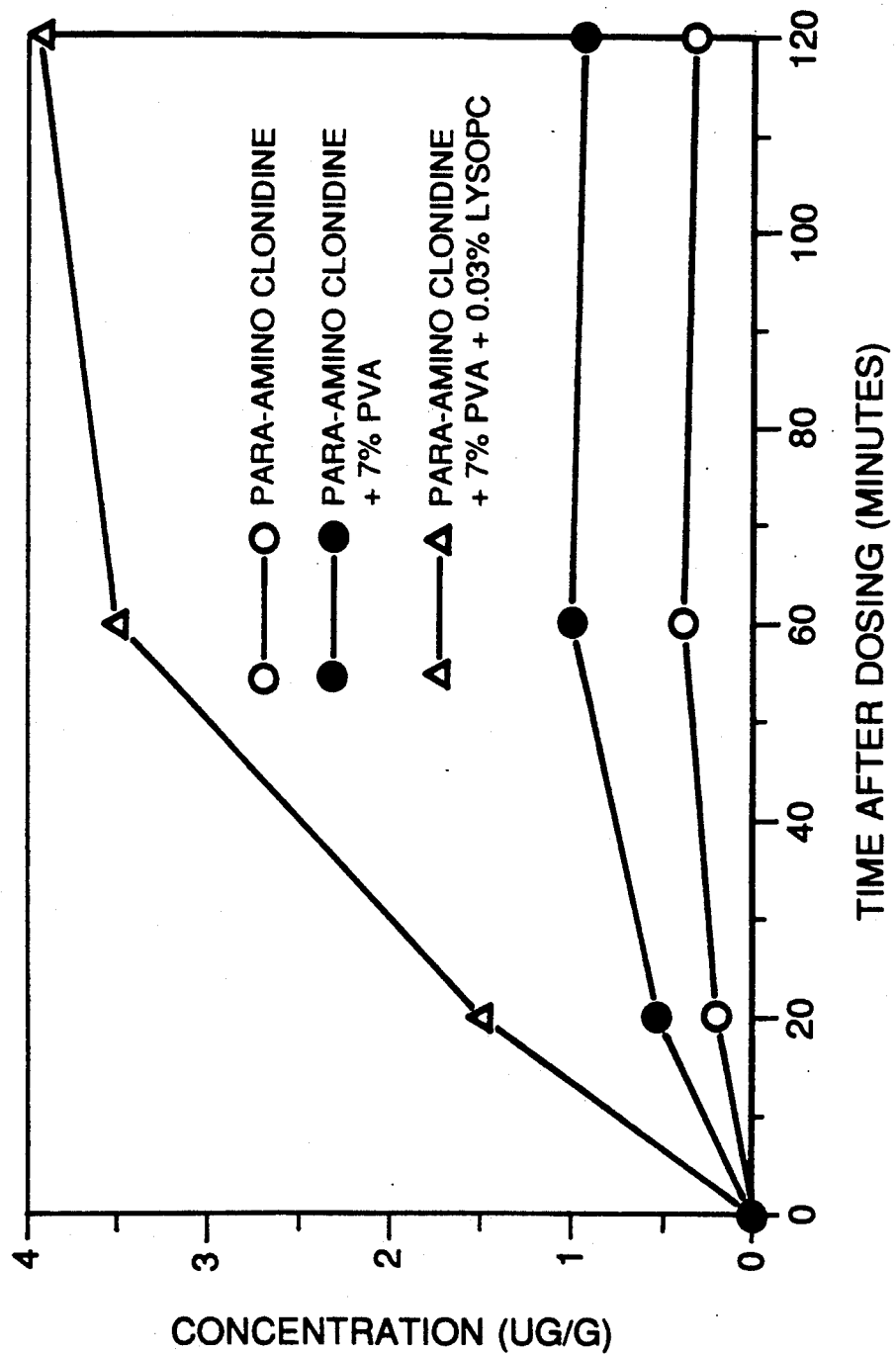
FIG. 2 compares the amount of a drug, para-aminoclonidine, found in the aqueous humor of rabbits which were administered the drug with polyvinyl alcohol (PVA), with lysopc and PVA and without either lysopc or PVA.

Twelve New Zealand albino rabbits were selected for evaluation of the penetration through the cornea of the para-amino-clonidine formulation set forth above. All rabbits received 30 μl of the 0.50% para-amino-clonidine topically in both eyes. Four rabbits were sacrificed at 20 minutes from dosing and their aqueous humor was withdrawn from their eyes. The aqueous humor was assayed by liquid scintillation counting to determine the amount of para-amino-clonidine in the aqueous humor. The same procedure was done on four different rabbits at 60 minutes from dosing and on another four rabbits, 120 minutes from dosing. Twelve control rabbits received 0.50% para-amino-clonidine as set forth in the formulation above without 0.03% lysopc and 7.0% PVA. Another 12 rabbits received 0.50% para-amino-clonidine as set forth in the formulation above without 0.03% lysopc. Aqueous humor was withdrawn and assayed as explained above. The results are shown in the graph depicted in FIG. 2. It can be seen from the graph that the amount of para-amino-clonidine in the aqueous humor is greater in the rabbits treated with the formulation containing PVA and PVA with lysopc. At 60 minutes there is almost a 2.5 fold and 10 fold increase in the amount of para-amino-clonidine found in the aqueous humor of those rabbits which received the drug in conjunction with PVA or with PVA and lysopc, respectively, versus those which received the drug without PVA or PVA and lysopc. The results indicate that lysopc has enhanced penetration of para-amino-clonidine through the cornea over PVA alone and para-amino-clonidine alone.

What is claimed is:

1. A method of enhancing the penetration of an ophthalmic drug through the cornea, which comprises:
topically applying to the eye an ophthalmic pharmaceutical composition comprising a therapeutically effective amount of the ophthalmic drug and an amount of a monoacyl phosphoglyceride effective to enhance corneal penetration of the drug.

2. The method of claim 1 wherein the monoacyl phosphoglyceride has the formula:

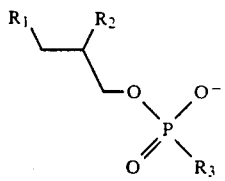

wherein, one of $R_1$ and $R_2$ is H or hydroxyl, thiol, amino, alkyl, alkoxy or alkyl sulfide and the other is an esterified, etherified or amidified aliphatic hydrocarbon group of 14 to 24 carbons, said aliphatic hydrocarbon group being substituted or unsubstituted, with zero to 5 double bonds, and which can be straight chain or branched, and may be substituted with one or more aromatic, cycloaliphatic or hydrophilic groups; and
$R_3$ is choline, O-$(CH_2)_3$-choline, O-glycerol, O-carnitine, O-inositol or O-lysophosphatidylglycerol.

3. The method of claim 1 wherein the monoacyl phosphoglyceride is selected from the group consisting of: lysolecithin, lysocardiolipin, lysodesoxylipids, lysophosphatidylinositol, lysophosphorylipids and α-lyso-r-O-alkyl or O-alkenyl phospholipids.

4. The method of claim 3 wherein the monoacyl phosphoglyceride comprises lysolecithin.

5. The method of claim 1 wherein the monoacyl phosphoglyceride concentration is about 0.001% to about 0.5%.

6. The method of claim 5 wherein the concentration is about 0.01 to 0.1%.

7. The method of claim 1 wherein the composition further comprises a polymer, protein or polypeptide in an amount sufficient to provide the composition with a viscosity of up to about 1000 cps.

8. The method of claim 7 wherein the composition phosphoglyceride is selected from the group consisting of: lysolecithin, lysocardiolipin, lysodesoxylipids, lysophosphatidylinositol, lysophosphorylipids and α-lyso-r-O-alkyl or O-alkenyl phospholipids.

9. The method of claim 8 wherein the polymer comprises hydroxypropylmethylcellulose.

10. The method of claim 9 wherein the monoacyl phosphoglyceride comprises lysolecithin.

11. The method of claim 10 wherein the lysolecithin concentration is between about 0.01% and 0.05% and the hydroxypropylmethylcellulose is present in an amount sufficient to provide the composition with a viscosity of between about 50 and 300 cps.

12. An improved topical, ophthalmic pharmaceutical composition comprising:
a therapeutically effective amount of an ophthalmic drug; and an amount of a monoacyl phosphoglyceride effective to enhance corneal penetration of the drug.

13. The topical ophthalmic composition of claim 12 wherein the monoacyl phosphoglyceride has the formula:

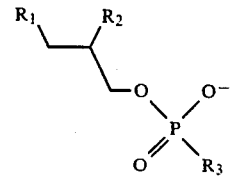

wherein,
one of $R_1$ and $R_2$ is H or hydroxyl, thiol, amino, alkyl, alkoxy or alkyl sulfide and the other is an esterified, etherified or amidified aliphatic hydrocarbon group of 14 to 24 carbons, said aliphatic hydrocarbon group being substituted or unsubstituted, with zero to 5 double bonds, and which can be straight chain or branched, and may be substituted with one or more aromatic, cycloaliphatic or hydrophilic groups; and
$R_3$ is choline, O-$(CH_2)_3$-choline, O-glycerol, O-carnitine, O-inositol or O-lysophosphatidylglycerol.

14. The composition of claim 13 wherein the monoacyl phosphoglyceride is selected from the group consisting of: lysolecithin, lysocardiolipin, lysodesoxylipids, lysophosphatidylinositol, lysophosphorylipids and α-lyso-r-O-alkyl or O-alkenyl phospholipids.

15. The composition of claim 14 wherein the monoacyl phosphoglyceride comprises lysolecithin.

16. The composition of claim 12 wherein the monoacyl phosphoglyceride concentration is about 0.001% to about 0.5%.

17. The composition of claim 16 wherein the concentration is about 0.01 to 0.1%.

18. The composition of claim 12 which further comprises a polymer, protein or polypeptide in an amount sufficient to provide the composition with a viscosity of up to about 1000 cps.

19. The composition of claim 18 wherein the composition comprises a polymer selected from the group consisting of alginates, carrageenan, guar, karaya, locust bean, tragacanth, xanthan, carbomer, hydroxyethylcellulose, hydroxypropylcellulose, hydroxypropylmethylcellulose, methylcellulose, polyvinyl alcohol, polyvinyl pyrrolidone, carboxymethylcellulose and agarose.

20. The composition of claim 19 wherein the polymer is hydroxypropylmethylcellulose.

21. The composition of claim 20 wherein the monoacyl phosphoglyceride comprises lysolecithin.

22. The composition of claim 21 wherein the lysolecithin concentration is between about 0.01% and 0.05% and the hydroxypropylmethylcellulose is present in an amount sufficient to provide the composition with a viscosity of between about 50 and 300 cps.

* * * * *